(12) United States Patent
Hawver

(10) Patent No.: US 8,816,291 B2
(45) Date of Patent: Aug. 26, 2014

(54) INDICIA FOR BACKSCATTER DETECTION IN PORTABLE RADIOLOGICAL DETECTORS

(75) Inventor: Jeffery R. Hawver, Marion, NY (US)

(73) Assignee: Carestream Health, Inc., Rochester, NY (US)

( * ) Notice: Subject to any disclaimer, the term of this patent is extended or adjusted under 35 U.S.C. 154(b) by 178 days.

(21) Appl. No.: 13/072,883

(22) Filed: Mar. 28, 2011

(65) Prior Publication Data

US 2012/0248321 A1    Oct. 4, 2012

(51) Int. Cl.
*H01L 27/146*    (2006.01)

(52) U.S. Cl.
USPC .................................................. 250/370.09

(58) Field of Classification Search
USPC .................................................. 250/370.09
See application file for complete search history.

(56) References Cited

U.S. PATENT DOCUMENTS

| 6,433,341 B1 | 8/2002 | Shoji | |
| 6,455,857 B1 | 9/2002 | Iwabuchi | |
| 6,977,988 B2 | 12/2005 | Niwa | |
| 7,053,378 B2 | 5/2006 | Yamamoto | |
| 7,317,190 B2 | 1/2008 | Ertel et al. | |
| 7,495,226 B2 * | 2/2009 | Jadrich et al. | 250/370.09 |
| 7,643,611 B2 | 1/2010 | Shedlock et al. | |
| 2004/0188626 A1 * | 9/2004 | Yamamoto | 250/370.09 |

FOREIGN PATENT DOCUMENTS

EP    2051109 A2    4/2009

OTHER PUBLICATIONS

International Search Report, International application No. PCT/US2012/028151, Dated Aug. 30, 2012, 2 pages.

* cited by examiner

*Primary Examiner* — Christine Sung

(57) ABSTRACT

Embodiments of secondary backscatter indicia; digital radiography detectors and radiographic imaging apparatus using the same; and methods for using the same can detect a secondary backscatter condition for a radiation exposure. In one embodiment, a DR detector can include a housing having first and second surfaces and a plurality of walls to form a cavity; a detector array mounted within the cavity to form an electronic radiographic image; and backscatter absorbing indicia distributed in a prescribed arrangement. Embodiments of methods and/or apparatus according to the application can detect secondary backscatter radiation, can notify a technician when secondary backscatter radiation is detected in an x-ray image or can detect and/or identify portions of an active imaging area of an x-ray detector subjected to secondary backscatter radiation.

20 Claims, 18 Drawing Sheets

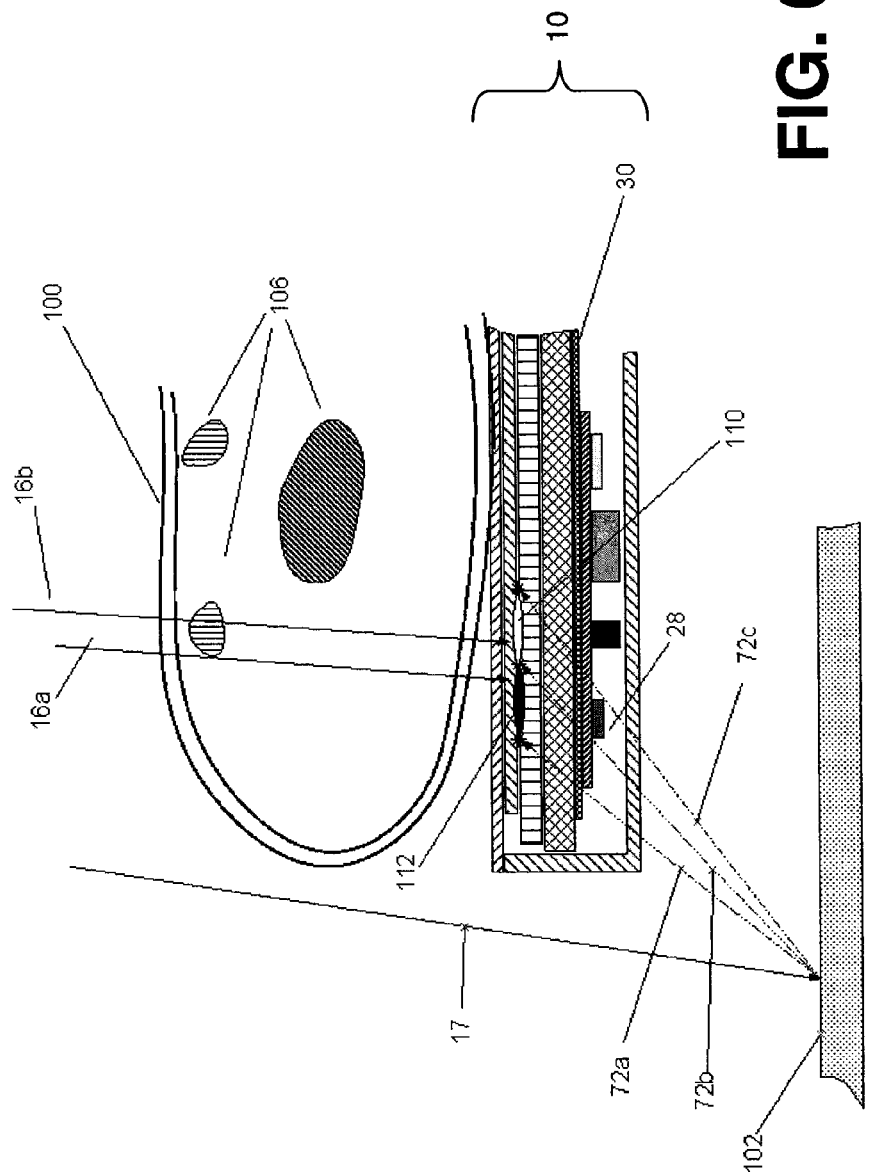

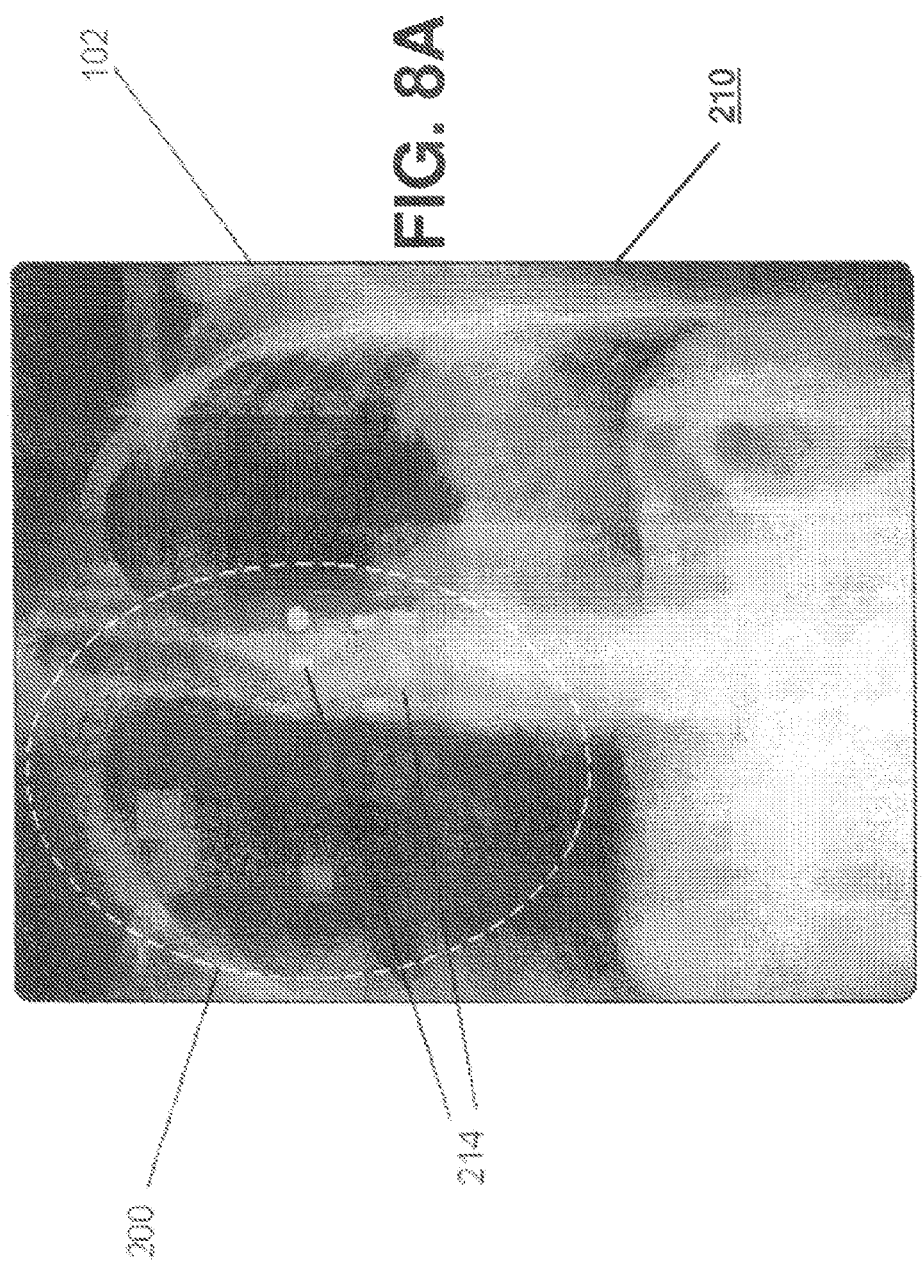

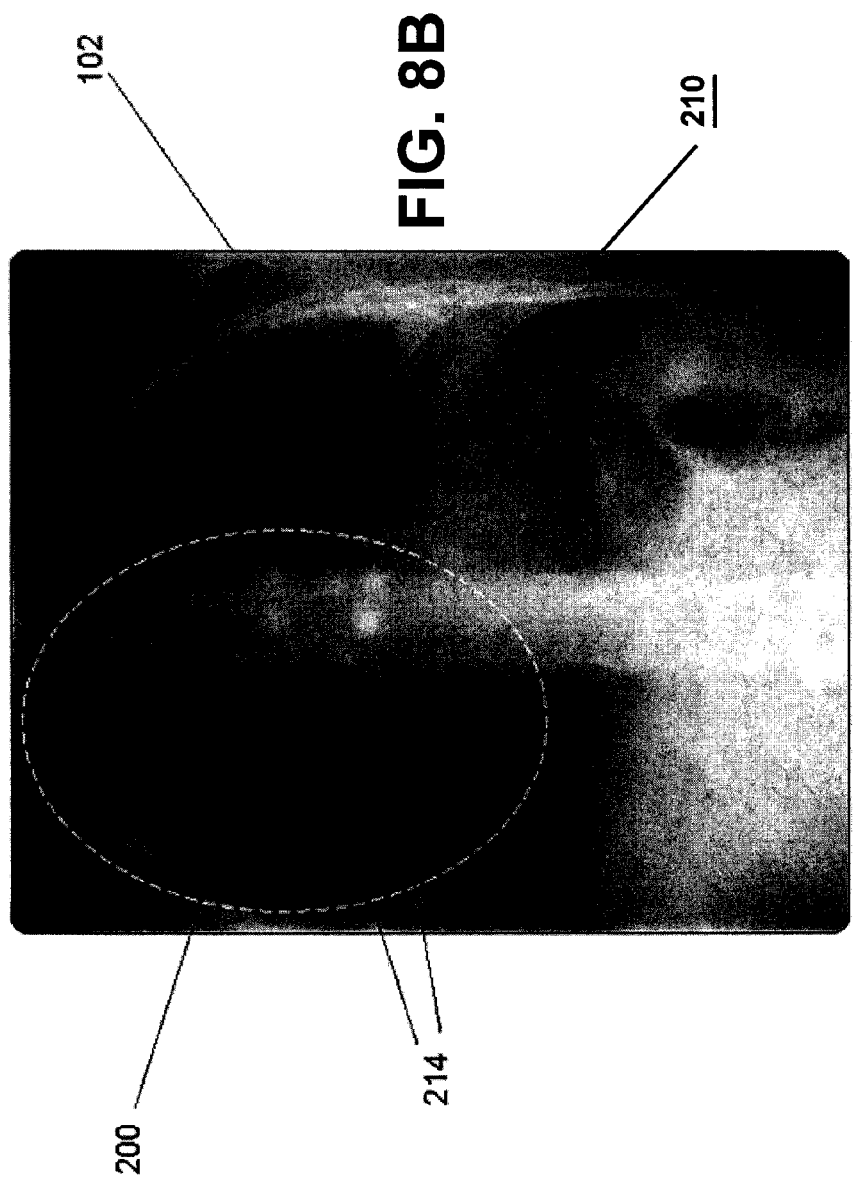

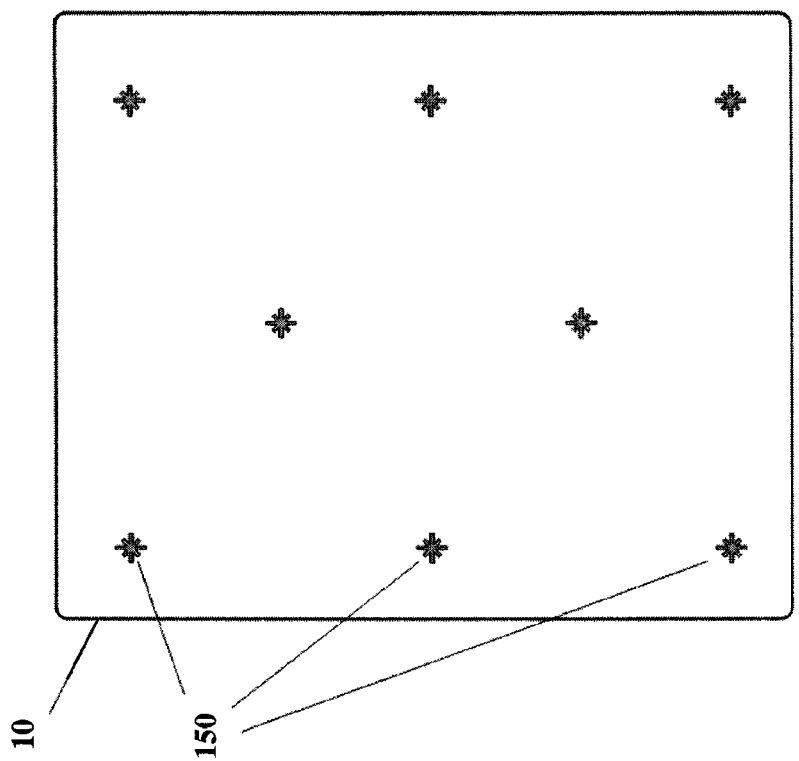

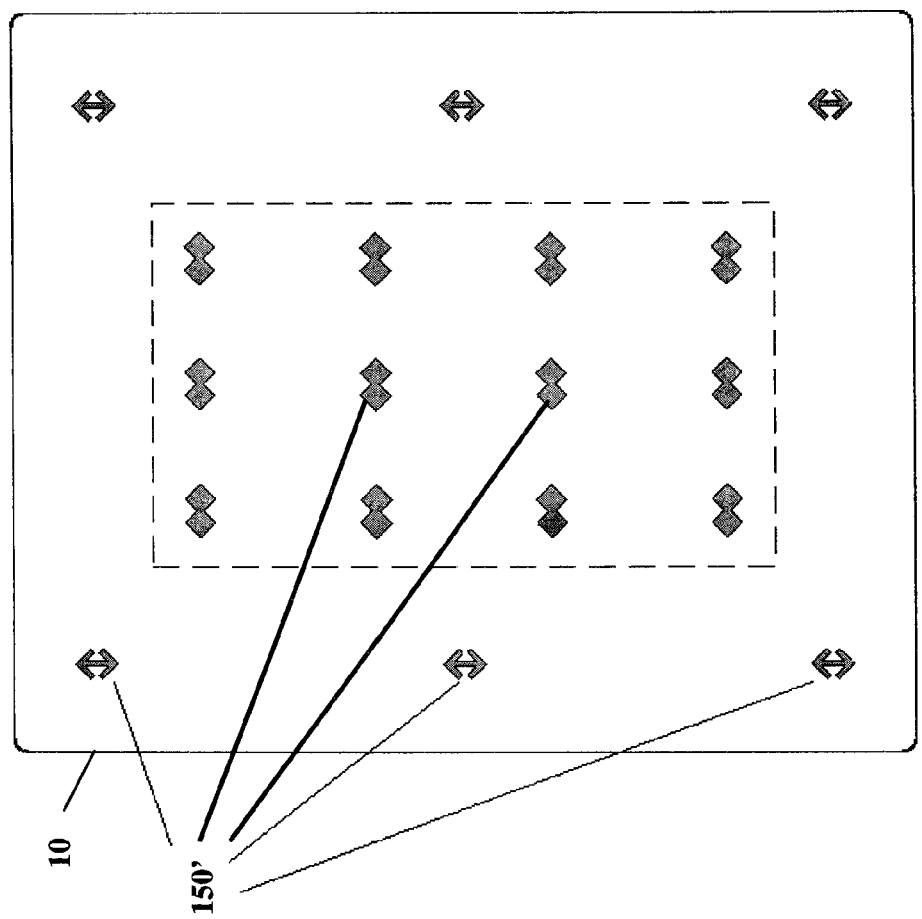

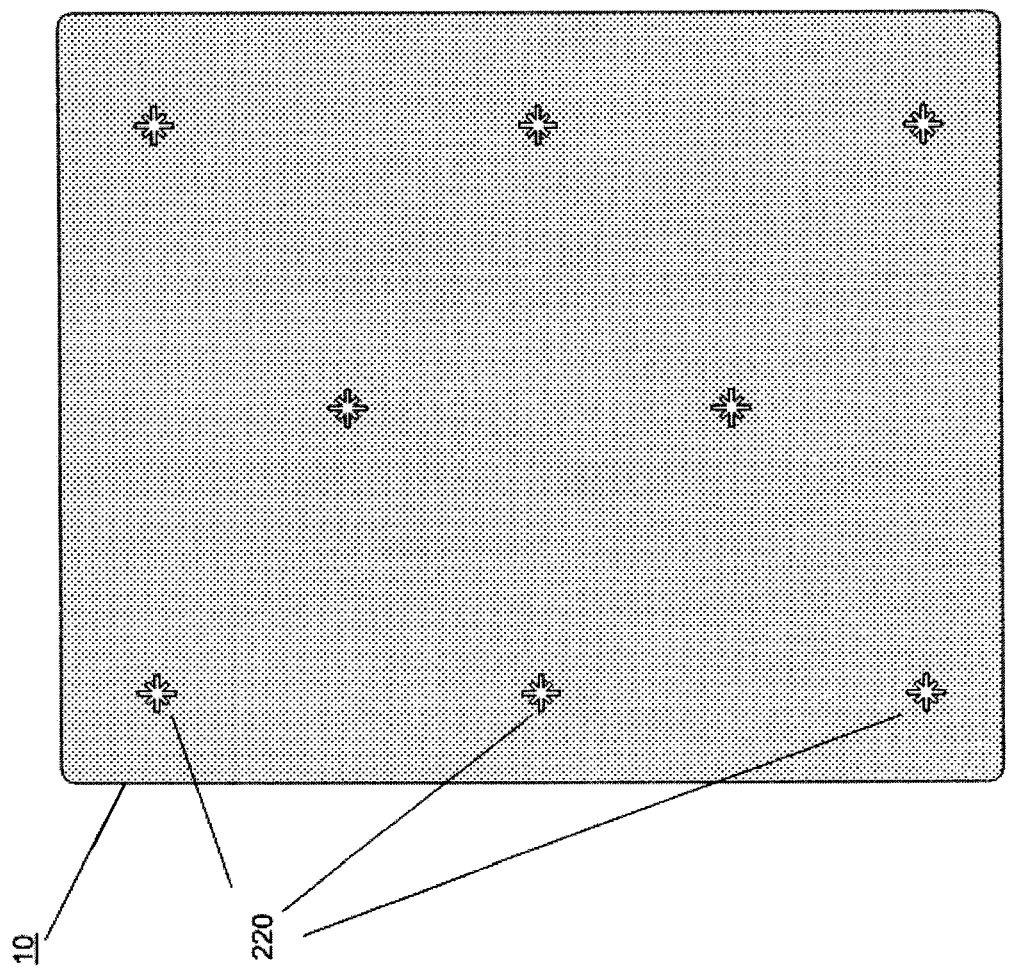

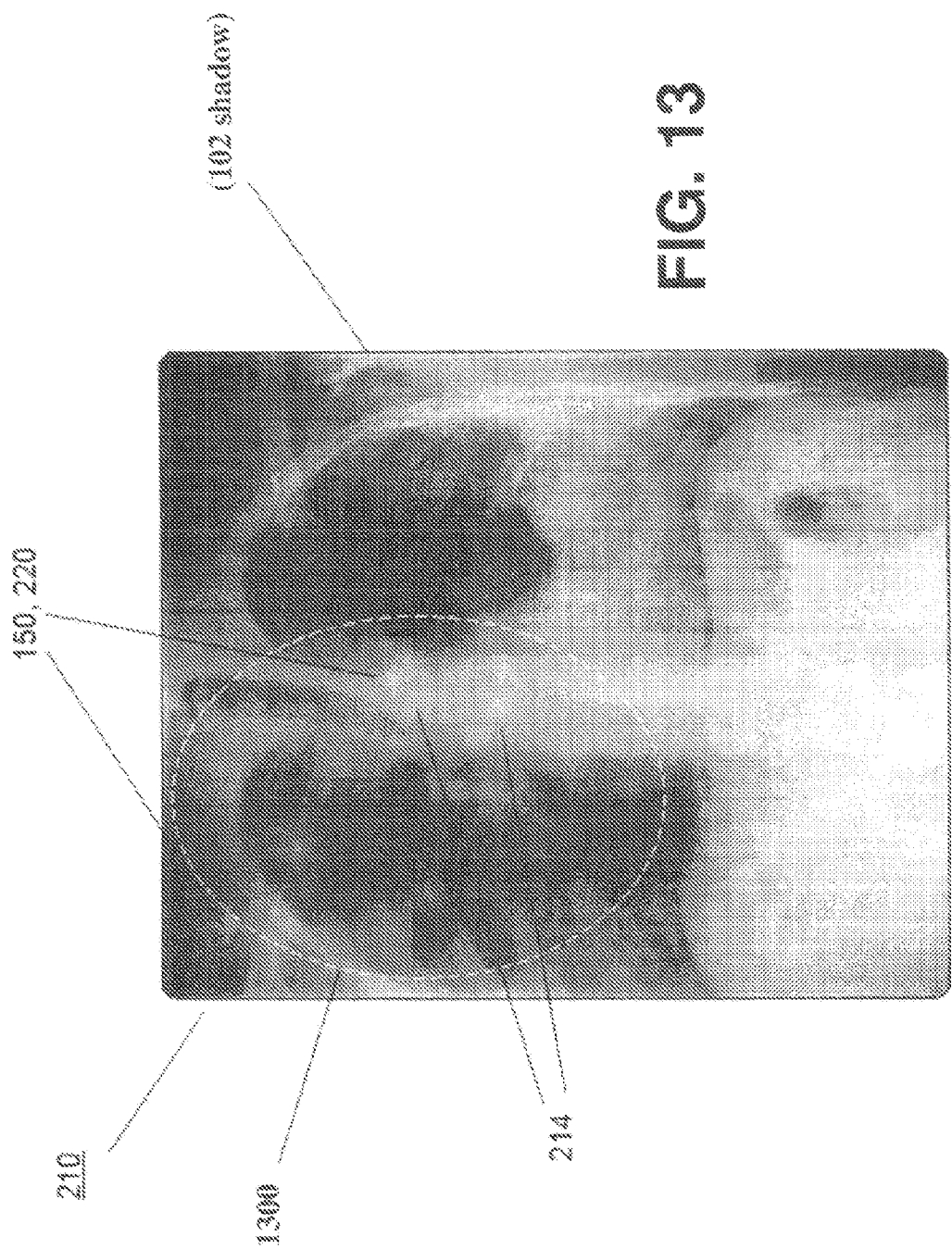

# INDICIA FOR BACKSCATTER DETECTION IN PORTABLE RADIOLOGICAL DETECTORS

FIELD OF THE INVENTION

The invention relates generally to the field of medical imaging, and in particular to radiographic imaging and digital radiographic (DR) detectors and more particularly to mitigation of potential loss of image quality in x-rays images intended for diagnostic purposes related to backscattering of x-ray fluence.

BACKGROUND

Stationary radiographic imaging equipment are employed in medical facilities (e.g., in a radiological department) to capture medical x-ray images on x-ray detector. Medical x-ray images can be captured using various techniques such as computed radiography (CR) and digital radiography (DR). Mobile x-ray apparatus are of particular value in intensive care unit (ICU) and other environments where timely acquisition of a radiographic image can allow an attending physician or clinician to have recent information on the condition of a patient or risks entailed in moving patients can be reduced.

Various U.S. patents address problems of x-ray backscatter and disclose various methods of reducing artifacts produced by x-ray backscatter. See for example, U.S. Pat. No. 7,053,378 Yamamoto, U.S. Pat. No. 6,433,341 Shoji, U.S. Pat. No. 6,455,857 Iwabuchi, or U.S. Pat. No. 7,317,190 Ertel et al.

However, there is a need for improvements in the consistency and/or quality of medical x-ray images, particularly when obtained by a mobile x-ray apparatus design to operate with a non-integrated x-ray detector.

SUMMARY OF THE INVENTION

An aspect of this application is to advance the art of medical digital radiography.

Another aspect of this application to address in whole or in part, at least the foregoing and other deficiencies in the related art.

It is another aspect of this application to provide in whole or in part, at least the advantages described herein.

An aspect of this application to is to provide methods and/or apparatus to address and/or reduce backscatter radiation problems caused by the use of portable (e.g., wireless) digital radiography (DR) detectors and/or mobile radiography imaging apparatus.

An aspect of this application to is to provide methods and/or apparatus that can detect backscatter radiation.

An aspect of this application to is to provide methods and/or apparatus that can notify a technician when secondary backscatter radiation is detected in an x-ray image (e.g., generated for medical diagnosis).

An aspect of this application to is to provide methods and/or apparatus that can detect and/or identify portions of an active imaging area of an x-ray detector (e.g., flat panel detector (FPD)) subjected to secondary backscatter radiation.

Another aspect of the application is to provide methods and/or apparatus by which radiography imaging apparatus can be retrofit with secondary backscatter radiation detection and secondary backscatter radiation image correction capabilities.

In accordance with one embodiment, the present invention can provide a method for identifying secondary backscatter in image data from a digital radiography (DR) detector, the method can include exposing a DR detector to x-ray flux; obtaining image data from the DR detector to form an electronic radiographic image corresponding to received x-ray flux; detecting representations of secondary backscatter indicia in the image data based on at least one characteristic of the secondary backscatter indicia in the DR detector; and detecting a secondary backscatter condition when the representations of the secondary backscatter indicia in the image data exceed a threshold.

In accordance with one embodiment, the present invention can provide a method for modifying a digital flat panel radiographic detector including a housing configured with first and second surfaces and a plurality of walls to form a cavity, a radiographic image detector mounted within the cavity to convert a radiographic image to an electronic radiographic image, the detector comprising a detector array; the method can include detecting a plurality of secondary backscatter indicia distributed in a prescribed arrangement in the cavity using positions of the secondary backscatter indicia and image data used to form the electronic radiographic image.

In accordance with one embodiment, the present invention can provide a digital radiography detector that can include a housing having first and second surfaces and a plurality of walls to form a cavity; a radiographic image detector mounted within the cavity to convert a radiographic image to an electronic radiographic image, the detector comprising a detector array formed on a substrate; and a plurality of backscatter indicia distributed in a prescribed arrangement in the cavity.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

FIG. 6 is a diagram that shows a portion of a cross section of an object, select internal components in a DR detector, and exemplary backscatter radiation according to embodiments of the application.

FIG. 8A is a diagram that shows an exemplary x-ray image with artifacts caused by secondary backscatter according to embodiments of the application.

FIG. 8B is a diagram that shows an exemplary x-ray image including blurred artifacts caused by secondary backscatter according to embodiments of the application.

FIGS. 11A-11B are diagrams that show an imaging area of a DR detector and exemplary distributions of backscatter indicia according to embodiments of the application.

FIG. 12 is a diagram that shows a DR detector including another embodiment of backscatter indicia according to the application.

FIG. 13 is a diagram that shows an exemplary x-ray image exhibiting secondary backscatter artifacts caused by internal electrical components and exemplary secondary backscatter artifacts caused by backscatter indicia according to embodiments of the application.

DESCRIPTION OF EXEMPLARY EMBODIMENTS

Figure 1:
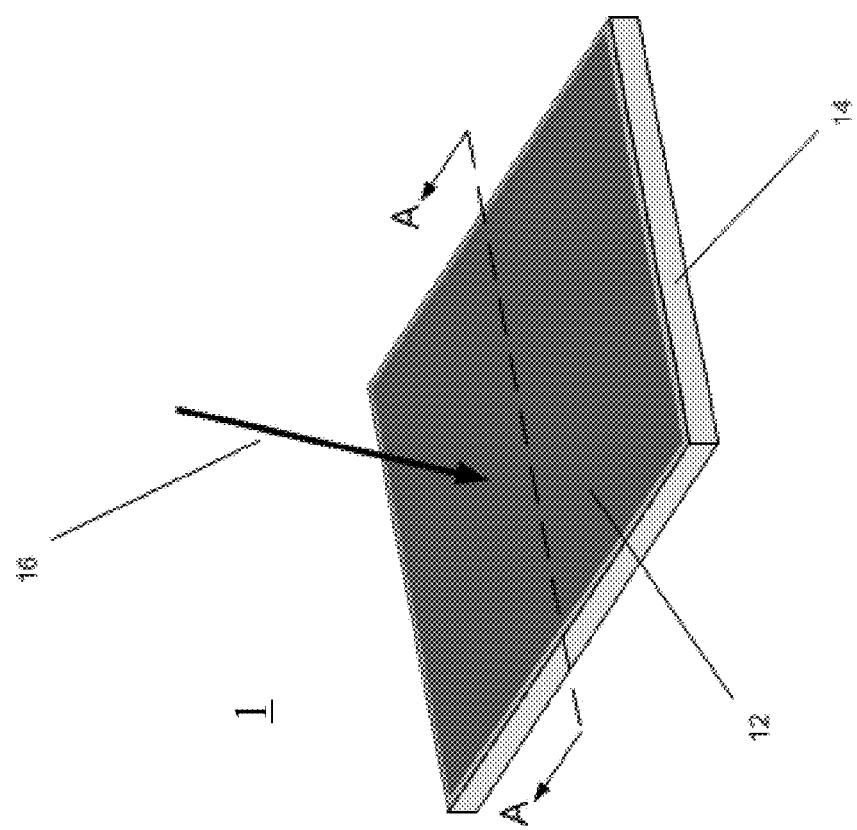
FIG. 1 is a diagram that shows a perspective view of a portable wireless DR detector that has utility in radiographic imaging apparatus applications.

The following is a description of exemplary embodiments of the invention, reference being made to the drawings in which the same reference numerals identify the same elements of structure in each of the several figures.

Where they are used, the terms "first", "second", and so on, do not necessarily denote any ordinal or priority relation, but may be used for more clearly distinguishing one element or time interval from another.

Figure 2:
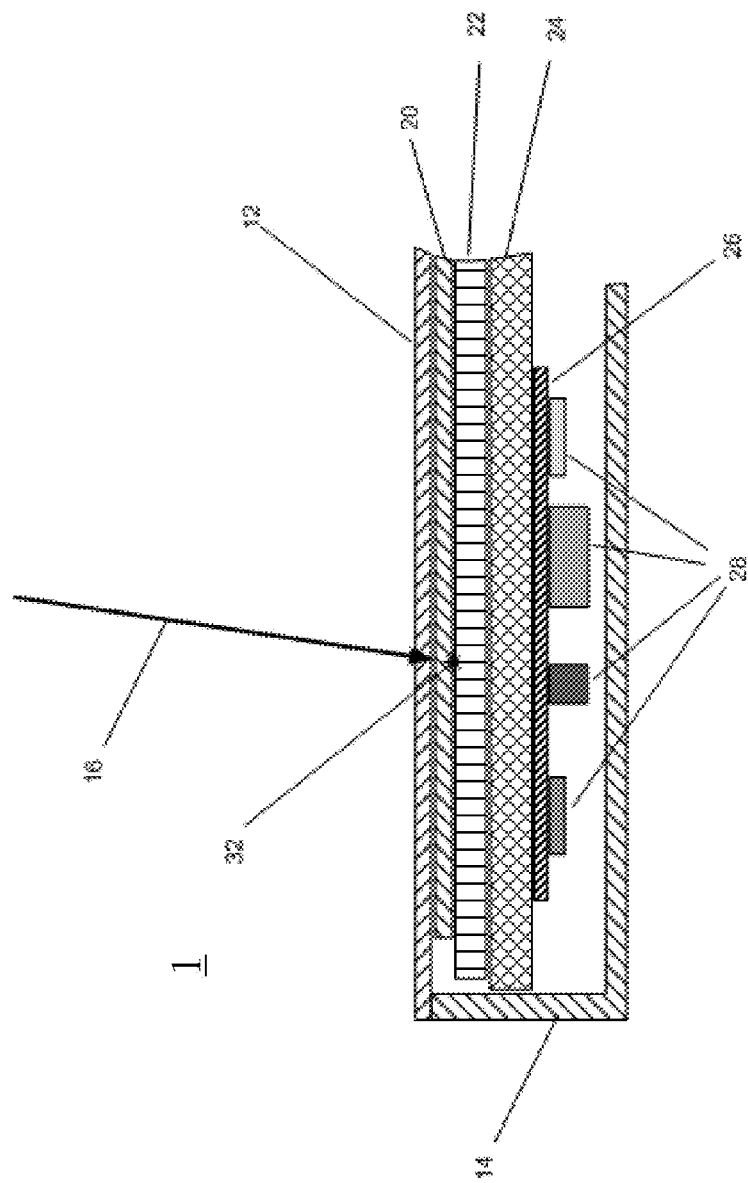
FIG. 2 is a diagram that shows a portion of a cross-sectional view along section line A-A of the portable wireless DR detector of FIG. 1.

FIG. 1 shows a perspective view of an exemplary related art portable wireless DR detector 1 that can have utility in radiography imaging apparatus applications. FIG. 2 shows a portion of a cross-section view along line A-A of the DR detector 1. As shown in FIGS. 1-2, the portable DR detector 1 can include an enclosure 14 that can support representative component elements of the DR detector 1 in operable positions for the operational functioning of the device. The enclosure 14 can made from materials that can be both rugged and/or lightweight. Materials that can be used in the enclosure 14 for this or other applications include, for example, aluminum, titanium and carbon fiber.

Top panel cover 12 can be rigidly or fixedly attached to the enclosure 14 and can be made of material that passes x-ray flux 16 without significant attenuation. For example, carbon fiber can be used for the top panel cover 12 because carbon fiber can have low absorption, lightweight and/or high strength. Scintillator 20 can be under (e.g., directly connected) the cover 12 to down-convert high-energy x-ray photons to lower energy photons to which an active sensing area of the DR detector 10 can respond. As shown in FIG. 2, x-ray flux 16 can pass through the top panel cover 12, impinge upon scintillator 20 where stimulation by high-energy photons in the x-ray flux 16 can cause the scintillator 20 to emit low energy photons 32.

Detector array 22, which can include an active sensing area, which can be under the scintillator 20, and preferably, in intimate contact with the scintillator 20, and readout electronics that can be co-planar with the detector array 22, partially below support member 24 or on a flexible connector therebetween. The detector array 22 can include a matrix of photosensitive pixels that convert photons to electric charge in a prescribed relation (e.g., direct proportion) to the number of photons emitted by the scintillator 20 under stimulation by the x-ray flux 16 (e.g., and received by the detector array 22).

Beneath the detector array 22, the support member 24 can be included to securely and/robustly mount the detector array 22. The support member 24 can be robustly attached to the detector housing that can form part of the enclosure 14 to assure that components within the enclosure 14 can remain securely or accurately positioned during handling and usage of the DR FPD. The support member 24 can further operate as a shock absorber between components therein and the enclosure 14.

Device electronics required for proper operation of the detector can be mounted within the enclosure 14 and can be beneath the support member 24. The electronics can include various electronic components 28 such as resistors, capacitors, diodes, integrated circuits, and the like, which are conventionally known and used by one skilled in the art. Electronic components 28 (e.g., processors, FPGAs, ASICs, chips, etc.) can be mounted on one or more separate and/or interconnected circuit boards 26.

Figure 3:
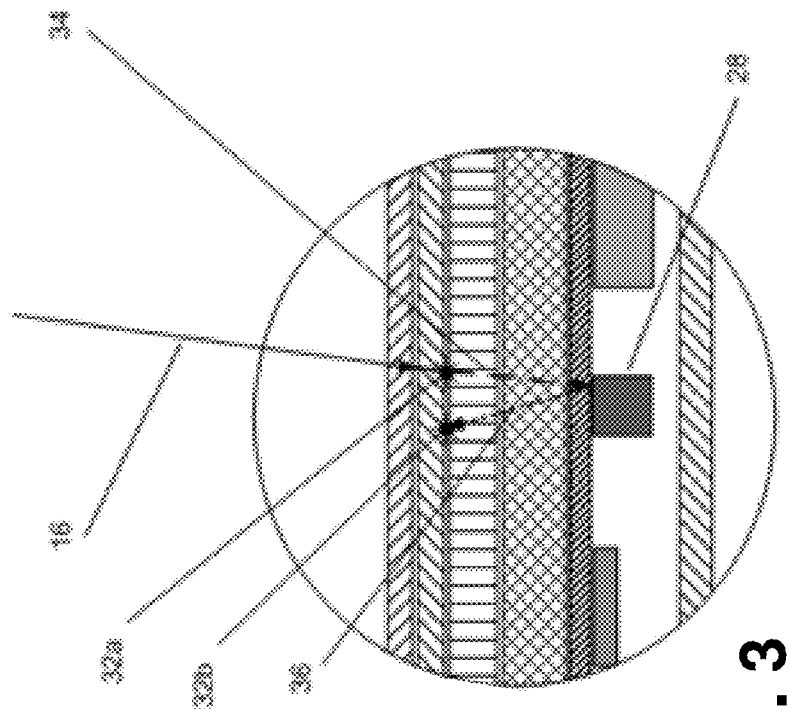
FIG. 3 is a diagram that shows a cross-sectional view that shows one type of backscatter condition that can result in degraded x-ray image quality in the flat panel detector of FIG. 1.

FIG. 3 is a diagram that illustrates a portion of FIG. 2 in an enlarged detail to describe one exemplary backscatter condition that can degrade x-ray image quality. As shown in FIG. 3, when x-ray flux 16 strikes the scintillator 20, photons 32a can enter detector array 22 and produce charge that can be readout from the detector 10 as image data at that pixel location. However, the scintillator 20 does not absorb all the energy in the x-ray flux 16 and a residual x-ray flux 34 can continue and pass through the scintillator 20 and elements below, such as the detector array 22, the support member 24 and the circuit board 26 where residual x-ray flux 34 can strike one or more of the electronic components 28.

A portion of the residual x-ray flux 34 can continue to pass through electronic component 28 and exit (not shown) through the back of the detector 1. Further, depending on various factors including type of device, material composition, and/or dimensions, the electrical component 28 can reflect a portion of the residual x-ray flux 34 that can propagate as reflected x-ray flux 36 back up through the detector array 22 to the scintillator 20. The reflected x-ray flux 36 can produce additional photons 32b that are emitted and absorbed by a different pixel(s) in the detector array 22, which will also be readout as image data. However, image data at pixel sites caused by additional photons 32b are not the result of the direct incident x-ray flux 16, and accordingly, can degrade image quality, for example, by introducing spurious information in the image. Such spurious information in the image can cause unacceptable artifacts.

Figure 4:
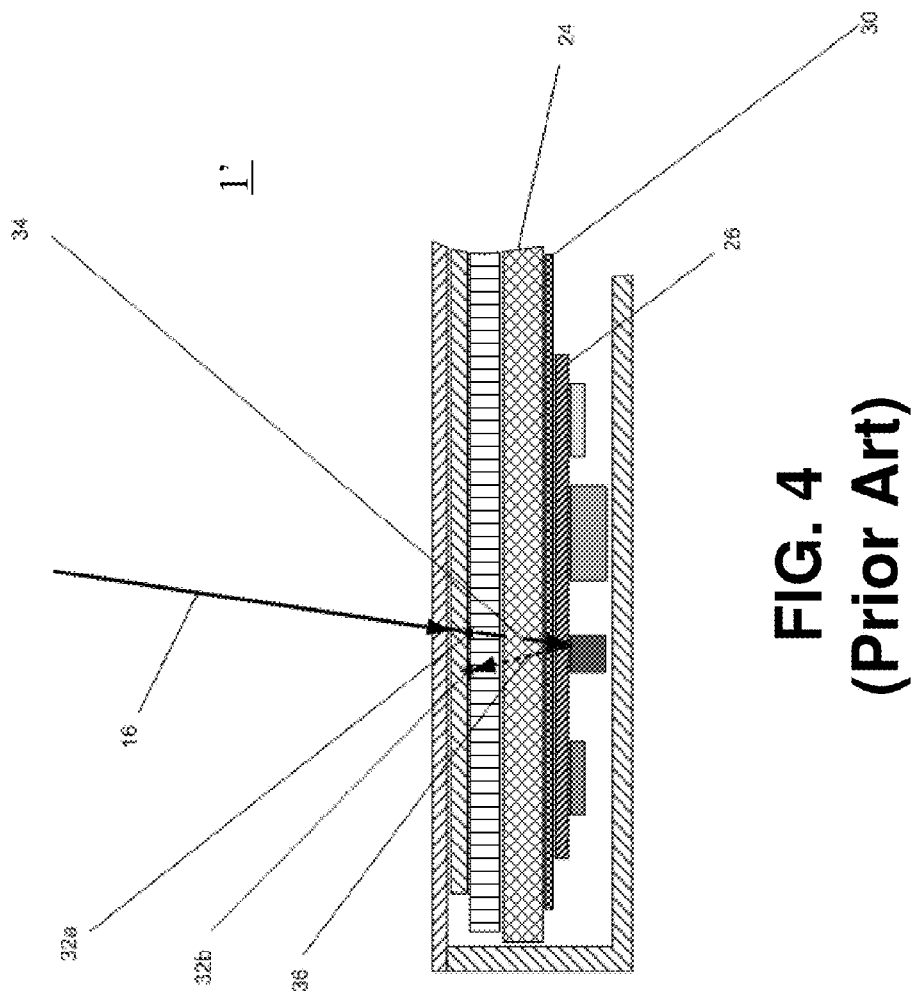
FIG. 4 is a diagram that shows one conventional solution to backscatter from internal structures and components in a DR detector.

FIG. 4 is a diagram that illustrates a conventional implementation to address backscatter from internal structures and components in a DR detector. As shown in FIG. 4, an additional component member can be added to a detector 1' to absorb reflected x-ray flux. The additional component can be a sheet of x-ray absorbing material 30. For example, the x-ray absorbing material 30 can be made from tungsten, lead or barium sulfate. The thickness of x-ray absorbing material 30

(e.g., 100 to 500 microns) can be made as thin as possible to reduce the overall weight of the DR detector 1'. As shown in FIG. 4, the reflected x-ray flux 36 travels back towards the scintillator 20 passing through the x-ray absorbing material 30 that can significantly attenuate the energy of the reflected x-ray flux 36 and thereby reduce a magnitude of spurious image information to an acceptable level.

Since wireless digital radiographic (DR) flat panel detectors (FPD), can be light weight and/or untethered, DR FPDs can be positioned behind and/or under patients in a bed, a wheel chair or the like without having to move the patient to a special table. However, an exact position of the DR FPDs under the patient may not be accurately or precisely known to an x-ray technician, which can complicate aiming of the generator head. To decrease a chance that the x-ray beam will miss a portion of the active sensing area of the detector, the technician may deliberately under collimate the x-ray to make sure the x-ray beam is wide/tall enough to expose the entire active area. An x-ray beam larger than the detector can have a detrimental effect on the quality of an x-ray image because of the x-ray backscatter from structures and objects behind the patient.

Additional sources and/or procedures can result in x-ray backscatter in a DR detector, which can detrimentally effect on the quality of an x-ray image. For the purposes of this application, two exemplary types of backscatter radiation can be identified and described, namely primary (e.g., first) backscatter radiation and secondary (e.g., second) backscatter radiation. Primary backscatter radiation can result from structures internal to a DR detector 10 and secondary backscatter can result from structures located outside of the DR detector 10 housing.

Figure 5A:
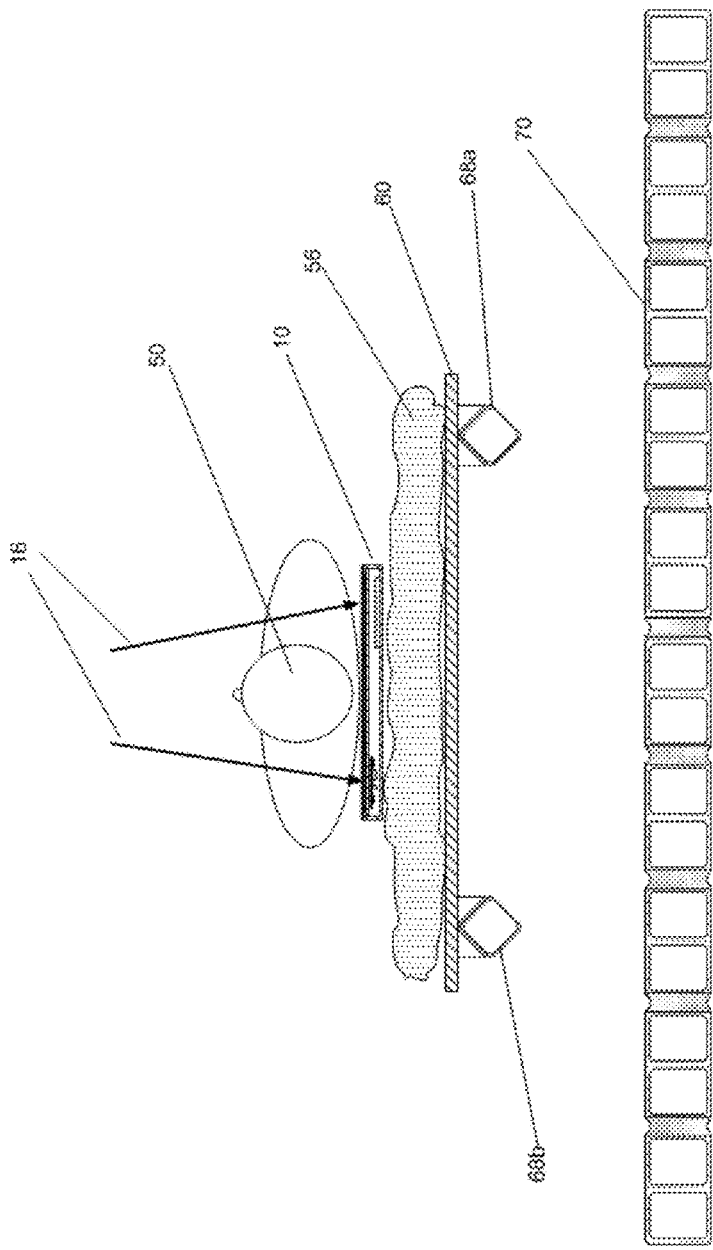
FIG. 5A is a diagram that shows an exemplary arrangement used at an x-ray imaging facility (e.g., an emergency room using a mobile radiography unit) according to the application.

FIG. 5A is a diagram that shows an exemplary radiographic imaging scenario that can be used in a medical facility such as an emergency room. The exemplary radiographic imaging scenario can include an object to be imaged, an x ray image sensor and x-ray flux 16 (e.g., an x-ray source) directed toward the image sensor such as a flat panel detector. As shown in FIG. 5A, patient 50 can recline on a bed structure 60 with mattress/pad 56. The bed structure 60 can be supported by frame rails 68a and 68b that are a structurally rigid material such as steel. Beneath frame rails 68a and 68b can be floor structure 70 that can include any number of materials such as poured concrete with rebar, cinder blocks, sub-flooring, framing materials, bricks, a solid metal floor or the like. An attachment for mounting the frame rails 68a and 68b to the floor structure 70 is not shown in FIG. 5A but can be conventional posts or leg supports, adjustable or fixed as known in the art.

As shown in FIG. 5A, the DR detector 10 can be positioned behind the patient 50 and incident x-ray flux 16 can be directed through the patient 50 into the DR detector 10. The DR detector 10 can be used as the DR detector 1, 1' described herein. One source of x-ray flux 16 can be a tube head and x-ray source components (not shown), which can be adjustably positioned (e.g., in 2D or 3D) relative to the patient 50.

However, as shown in FIG. 5A, an exact placement of the DR detector 10 can not be readily ascertained by the x-ray technician because the DR detector 10 can be obscured by the patient 50. To ensure the x-ray flux 16 impinges or fills the full imaging area of the DR detector 10, the technician can, either intentionally or unintentionally, overfill the target area by opening a collimator at the tube head too much, which can result in the x-ray flux encompassing an area beyond/outside the DR detector 10. By overfilling the target area, the technician can assure the x-ray DR detector 10 can be fully exposed; however, overfilling can create additional disadvantages such as x-ray radiation (e.g., extraneous x-ray flux 17) that can scatter/reflect off structures that can be positioned behind the patient 50. Overfilling can cause secondary backscatter radiation.

Figure 5B:
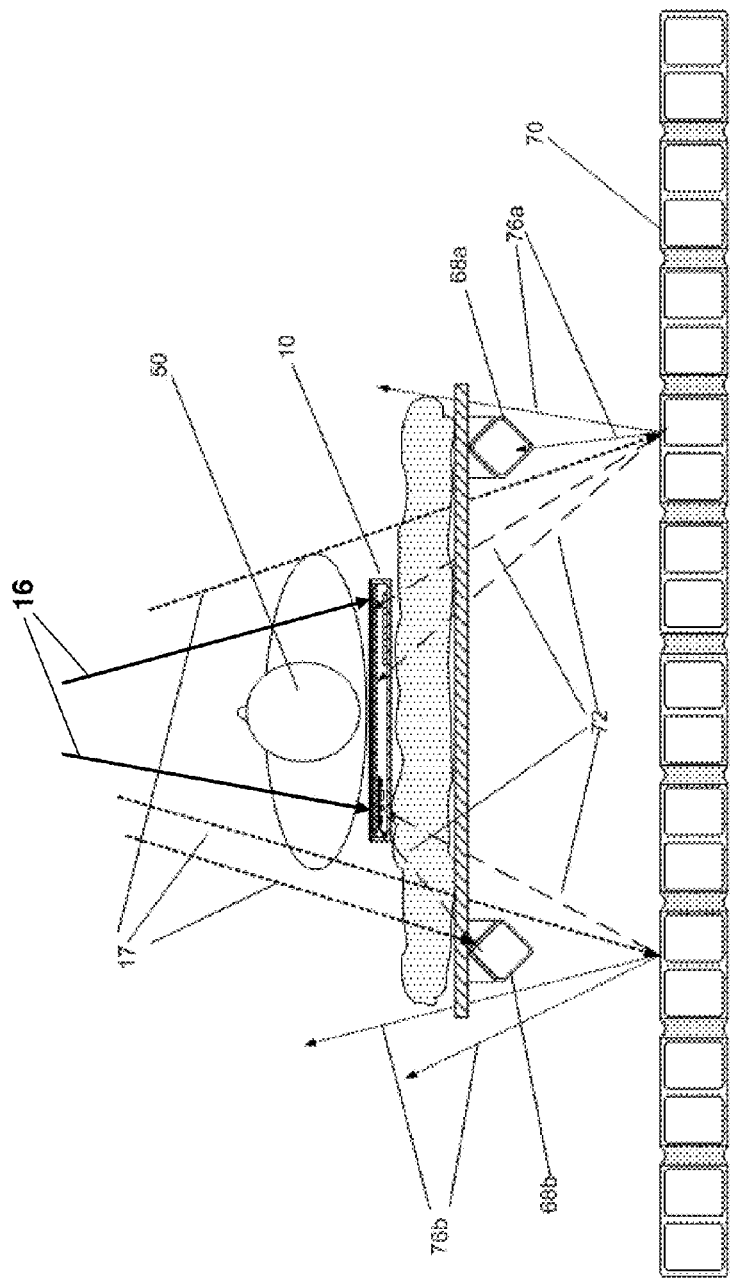
FIG. 5B is a diagram that shows the exemplary arrangement of FIG. 5A including additional incident x-ray flux (e.g., extraneous x-ray flux) according to the application.

FIG. 5B is a diagram that illustrates representative implications of secondary backscatter radiation according to the application. FIG. 5B illustrates additional incident x-ray flux or extraneous x-ray flux 17. The extraneous x-ray flux 17 can be produced by the x-ray generator, however, the extraneous x-ray flux 17 falls beyond the boundary of DR detector 10, does not impinge the DR detector 10, and preferably, does not produce any image information. Further, the extraneous x-ray flux 17 should be reduced or minimized to reduce the risk of exposure of x-rays to unintended parts of the body and/or to reduce the risk of exposure of x-rays to the administering technician.

As shown in FIG. 5B, in many cases extraneous x-ray flux 17, for example, does not pass through the patient 50 and therefore can experience less or very little attenuation relative to incident (e.g., direct) x-ray flux 16 that can be partially or mostly absorbed by the body of the patient 50 and/or the DR detector 10. The extraneous x-ray flux 17 can pass through the mattress 56 and/or bed structure 60 until the extraneous x-ray flux 17 ultimately impinges a material that reflects the extraneous x-ray flux 17 (e.g., back in the direction of the x-ray source or the DR detector 10). For example, as shown in FIG. 5B, when the extraneous x-ray flux 17 impinges the bed rail 68b and the floor structure 70, two types of secondary backscatter can occur. The first type is non-detected backscatter flux 76a and 76b that is reflected in a direction that does not impinge the DR detector 10 and therefore can not be detected as image data by the DR detector 10. The second type is detected backscatter flux 72 that is reflected in a direction that impinges the DR detector 10 and can produce image data. For example, the detected backscattered flux 72 can reflect up through the bed structure 60, through the mattress 56 and through the enclosure of the DR detector 10. Detected backscattered flux 72 can include radiation that can enter the DR detector 10 and produce erroneous image information. Thus, not all secondary backscatter radiation or x-ray flux hits the DR detector 10. Much or perhaps most of the extraneous x-ray flux 17 that hits various structures behind the patient 50 can scatter away from the DR detector 10. Non-detected backscatter flux 76a and 76b (e.g., secondary backscatter radiation) is not a concern with regard to image degradation or image data artifacts because the non-detected backscatter flux 76a and 76b does not enter the DR detector 10. Again, in embodiments according to this application, the secondary backscatter radiation can be scattered from a source outside the enclosure of the DR detector 10. The secondary backscatter radiation scattered from the source outside the enclosure of the DR detector 10 can be subsequently additionally reflected and/or scattered by structures internal to the DR detector 10.

FIG. 6 is a diagram that shows a side view of a cross section of a patient anatomical portion 100 including several internal anatomical structures 106 that can be x-rayed for examination, a portion of the DR detector 10 including representative internal components, and a backscatter producing structure 102 below (e.g., opposite the patient) the DR detector 10. As shown in FIG. 6, the incident x-ray flux 16 can be divided into two exemplary components: x-ray flux portion 16a and x-ray flux portion 16b. When the incident x-ray flux portion 16b enters the anatomical portion 100 and passes through one of the anatomical structures 106, the incident x-ray flux portion 16b can be attenuated in proportion to the density of the anatomical structure's material. The incident x-ray flux portion 16a passes adjacent to the same one of the anatomical structure 106, but is not attenuated to the same degree as the x-ray flux portion 16b. When x-ray flux portions 16a and 16b impinge the scintillator 20, photons can be generated in proportion to the respective energy of x-ray flux portions 16a and 16b. Since x-ray flux portion 16b has been attenuated more than x-ray flux portion 16a by the anatomical structure, the image data readout from the DR detector 10 will show image density changes at those pixel locations. Such density changes can indicate a boundary of the anatomical structure (e.g., the anatomical structures 106). The shape, appearance and/or size as revealed in the derived image data can be used to diagnosis any abnormality in one of anatomical structures 106 in the patient 50.

As shown in FIG. 6, the extraneous x-ray flux 17 that impinge backscatter producing structure 102 can produce detected backscatter flux 72a, 72b and 72c, which can pass through the back of the DR detector 10. The region 112 between detected backscattered flux 72a and 72b is shown as an exemplary location where flux passes through internal components without hitting the electrical components 28, and accordingly can impinge the scintillator 20 and stimulate photon emission in the region 112. Such photons generated by secondary backscatter radiation can add to photons already created by direct incident x-ray flux portion 16a (e.g., from the x-ray generator) or nearby x-ray flux 16 that have passed through the anatomical portion 100.

A different situation that can occur is illustrated in the area between detected backscatter flux 72b and 72c that strikes the electrical component 28, which can attenuate backscatter flux (e.g., more attenuation than in the region 112). The detected flux 72b and 72c can impinge the scintillator 20 at the region 110, however, since this backscattered radiation of the detected flux 72b and 72c has been attenuated by the electrical component 28 the resulting number of photons caused to be emitted can be much less than in the region 112. Such different paths through the DR detector 10 by the secondary backscattered radiation can effect/alter image data associated with the anatomical structure 106 of the anatomical body 100 in pixels of the region 110 and in particular with regard to the edge boundary definitions and/or appearance of the anatomical structure 106. Such representative examples of secondary backscatter radiation are described to illustrate effects and serious implications of extraneous x-ray flux and detected backscattered radiation, which can introduce image data errors that can interfere with radiographic diagnostic image evaluation.

Embodiments of apparatus and/or methods according to the application can provide a capability to detect and/or correct detrimental effects or image artifacts caused by secondary backscatter radiation for a DR detector or radiographic imaging apparatus (e.g., portable) using the same. Embodiments of apparatus and/or methods according to the application can provide a capability to determine if an x-ray image has subtle artifacts from backscatter radiation.

Figure 7:
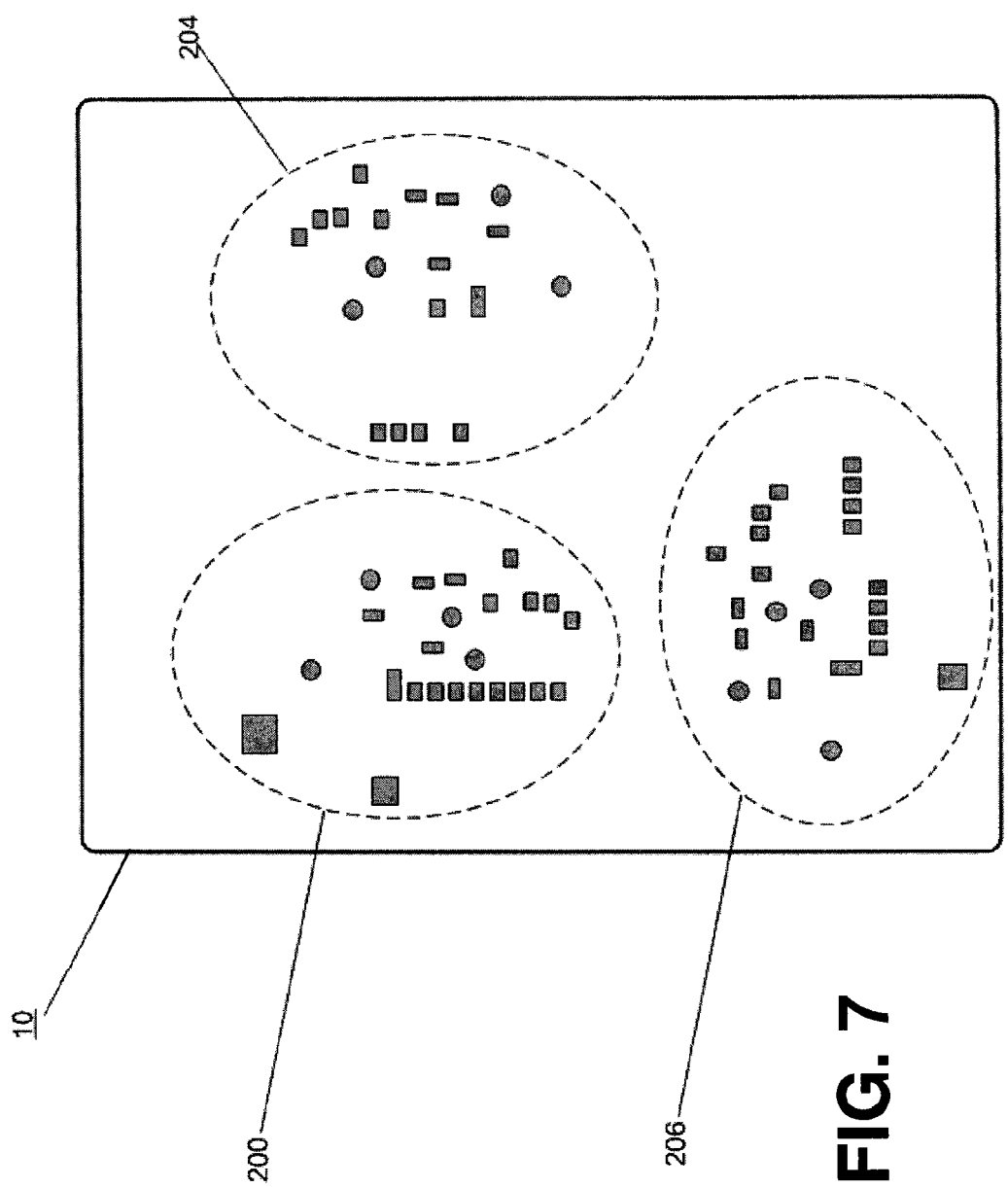
FIG. 7 is a diagram that shows an exemplary embodiment of a component image map showing the location of electronic components within a DR detector according to the application.

FIG. 7 is a diagram that illustrates an embodiment of a component image map showing an exemplary layout or location of selective components (e.g., components 28 in FIG. 2,) within the DR detector 10. The components placement/location in the component image map appear as viewed through the top cover 12 of the DR detector 10. As shown in FIG. 7, groups of electronic components are labeled as clusters 200, 204 and 206, respectively. In one embodiment, each cluster can be associated with a different circuit board or function such as the digital readout electronics or power supply circuitry, for example. However, there is no distinguishing difference between components in each of the clusters 200, 204 and 206; the purpose is to illustrate that there can be multiple different clusters of components placed inside of the DR detector 10. In one embodiment, electronic components in the clusters 200, 204 and 206 are elements that have a density or absorption of x-ray flux over a threshold value.

Such an exemplary component image map of this kind can be produced using various detector manufacturing component configuration diagrams or by placing the DR detector 10 with the backside facing towards the x-ray tube head while firing the x-ray generator. This exemplary latter empirical technique can simulate a backscatter condition using the direct x-ray beam (e.g., incident x-ray flux 16) and can image all internal devices and mechanical components. Unintended secondary backscatter radiation can produce subtle density variations in an image caused by the electronic components 28 or components in the component image map within the DR detector 10. Such subtle density variations in an image caused by secondary backscatter radiation impinging the components within the DR detector 10 typically do not look exactly like the component image map because, unlike the direct x-ray flux produced component image maps, the secondary backscattered radiation can be very non-uniform in energy and direction. The resultant artifacts produced by secondary backscatter radiation through components of the DR detector 10 have a prescribed relationship to corresponding components in the component image map. However, the resultant artifacts produced by secondary backscatter through components of the DR detector 10 tend to be blurry and because the secondary backscatter can occur at oblique angles, the component shadows can have differing relative sizes/shapes, can be displaced from or displaced relative to corresponding positions in the component image map and/or can occur in a portion of the DR detector 10.

FIG. 8A is a diagram that illustrates an exemplary simulated x-ray image including artifacts caused by secondary backscatter. As shown in FIG. 8A, only components from cluster 200 appear and components from clusters 204 and 206 do not effect an x-ray image 210. The exemplary x-ray image shown in FIG. 8A can occur because of the unpredictable non-uniform nature of the distribution of secondary backscatter radiation. Individual component shadows 214 of cluster 200 appear superimposed over the regions of the spine in x-ray image 210. In actual x-ray images with artifacts from secondary backscatter, the component shadows tend to be less defined with blurred edges. The component shadows that are sharp and well defined can be a better situation since it is more likely that an artifact of this type could be identified as such rather than mistaken for a disease feature.

FIG. 8B is a diagram that illustrates the exemplary simulated x-ray image of FIG. 8A including blurred artifacts caused by secondary backscatter, although the effects of the component shadows can be even more subtle. An amount of blurring in artifacts can be related to a distance to the scintillator 20. Thus, blurred artifacts more typically result from the conditions that generate secondary backscatter radiation. As shown in FIGS. 8A-8B, the image artifacts caused by secondary backscatter radiation striking components in the DR detector 10 can be a major concern and can result in misdiagnosis in radiological examinations.

Figure 9:
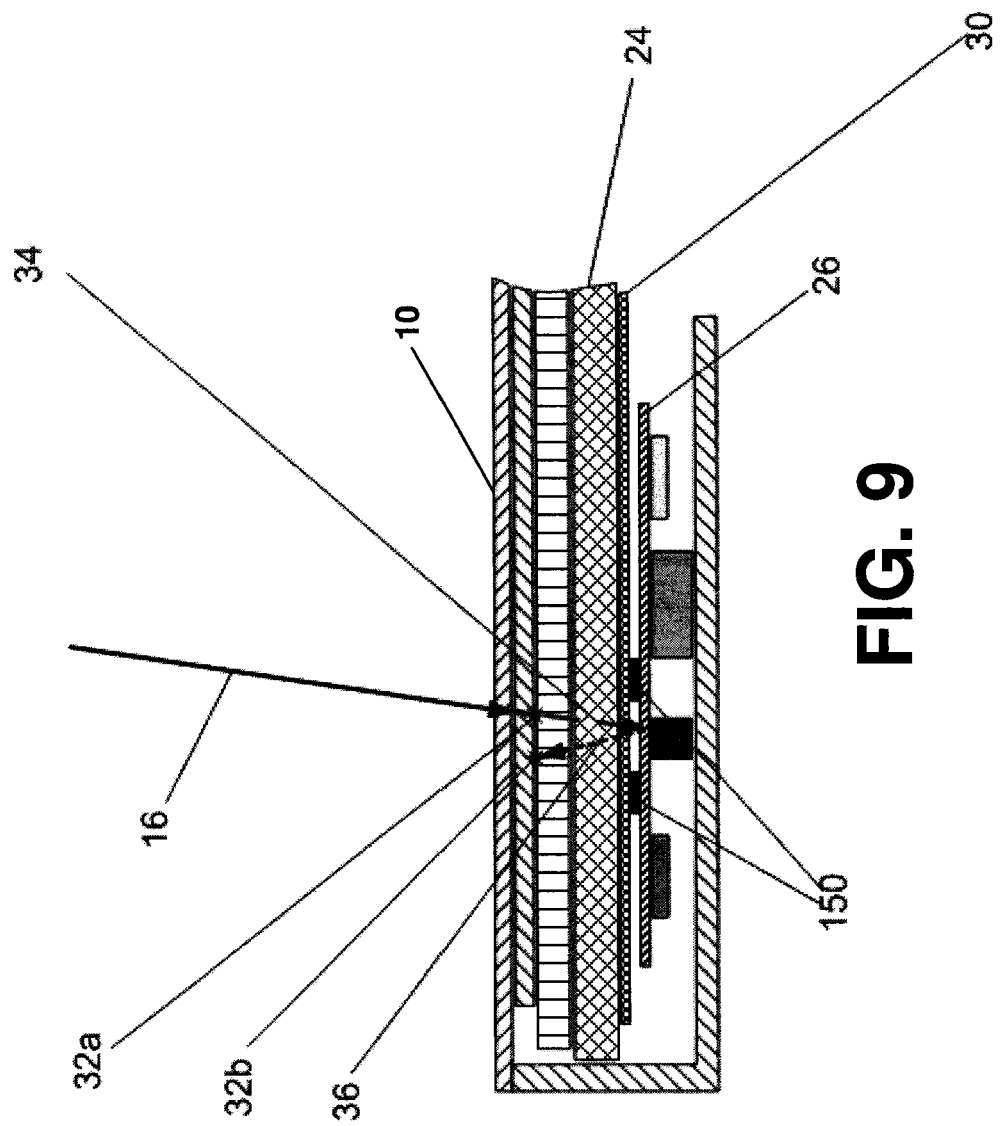
FIG. 9 is a diagram that shows a cross-sectioned view of a portion of a DR detector including an embodiment of backscatter indicia according to the application.

FIG. 9 is a diagram that shows a cross-sectioned view of a portion of an embodiment of a DR detector including backscatter indicia according to the application. As shown in FIG. 9, backscatter indicia 150 can be added between circuit board 26 and x-ray absorbing material 30, which can be used to reduce primary backscatter effects. Backscatter indicia 150 can be small markers that can react (e.g., absorb, pass or are opaque) to x-ray radiation and can produce predictable and identifiable shadows in x-ray images when secondary backscatter radiation is present. Opaque backscatter indicia can be made from the same type of materials identified for x-ray absorbing material 30. In one embodiment, lead or tungsten can be preferred for the opaque backscatter indicia 150. The backscatter indicia material can produce a high contrast shadow image in the x-ray image when secondary backscatter radiation is present. For example, the backscatter indicia material can be made as thick as practicable to absorb secondary backscatter radiation to increase the backscatter indicia shadow image contrast or to guarantee the shadow image produces high contrast.

In one embodiment, size and/or positions of the backscatter indicia 150 can be determined based on attenuation (e.g., density, material and thickness), available space (e.g., thickness between components 28 and the upper or lower surface of the detector 10), distance to the scintillator and overall weight of the backscatter indicia 150. For example, the backscatter indicia 150 can be between 0.1 cm, 0.5 cm, 1 cm, 2 cm or greater than 3 cm in width or length. Further, the backscatter indicia 150 have an x-ray attenuation characteristic independent of or related to an x-ray attenuation characteristic of a selected electronic component (e.g., greater than the electronic components. 2× greater or 5× greater). In one embodiment, the backscatter indicia 150 can have an x-ray attenuation characteristic related to the object(s) to be imaged.

Figure 10:
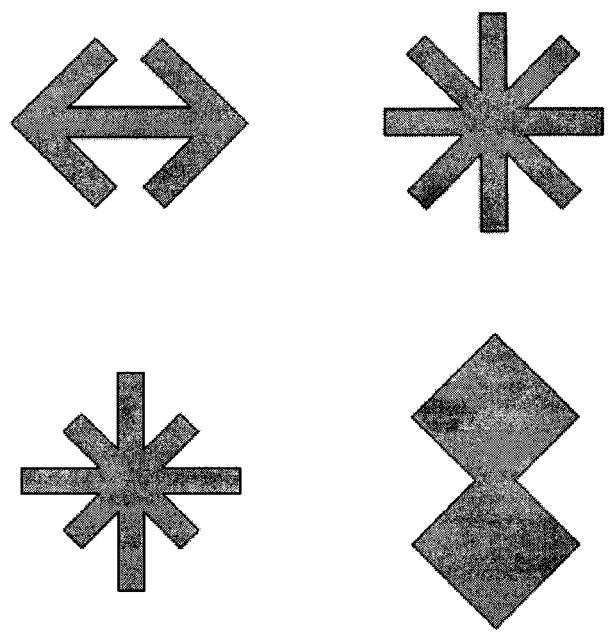
FIG. 10 is a diagram that shows exemplary backscatter indicia shapes according to embodiments of the application.

FIG. 10 is a diagram that shows exemplary backscatter indicia shapes according to embodiments of the application. FIG. 10 shows non-limiting example shapes that can be used for the backscatter indicia 150. One purpose of the exemplary unique indicia shape is to make the backscatter indicia 150 readily identifiable visually, either with the eye or by a suitable computer operable image processing algorithms that can process the image data and detect when backscatter indicia 150 shadows are present (e.g., based on known positions, sizes, shapes, density, etc. of the backscatter indicia 150). Thus, in one embodiment, the secondary backscatter indicia can include a prescribed arbitrary shape, where the prescribed arbitrary shape includes visually distinctive shape relative to an object being imaged. Exemplary prescribed arbitrary shapes can include, but are not intended to be limited to a starburst, a star, multiple oblique angles, an arrow, or an alphanumeric character.

When backscatter indicia 150 can be detected in an image (or image data) then that detection can be an indication that secondary backscatter occurred during exposure of the patient during the examination and that there can be subtle electrical component shadows in the image that can cause diagnostic errors. Using such an exemplary procedure or using such an indication when backscatter artifacts are detected in a particular x-ray image, the particular x-ray image can be flagged or marked appropriately to warn the technician at the time of the exposure and/or warn the radiologists/doctors for subsequent diagnosis. Alternatively or in addition, a warning indicator can be used (e.g., displayed) at a control console. In one embodiment, the warning indicator at the control console can be used to prevent further action until acknowledged by the technician. Exemplary backscatter detection indications according to embodiments of the application can allow for appropriate action to be taken to correct the situation such as placing an attachable lead shield or lead pad behind the detector, closing down the shutters to reduce or prevent extraneous x-ray flux, more accurately aligning the detector to the x-ray flux, or the like. In select situations, remedial actions resulting from the detected backscatter detection indications can result in the patient being exposed to another x-ray dose.

According to embodiments of the application, the size of backscatter indicia 150 can also be appropriately chosen so that shape of the markers can be sufficiently resistant to blur by the diffuse secondary backscatter radiation to allow reliable detection, for example, by the eye or by a suitable image processor imaging algorithms.

Further according to embodiments of the application, because of the non-uniformity of distributions of secondary backscatter, the backscatter indicia 150 can be distributed throughout the DR detector 10 (e.g., the entire active imaging area) so that an accurate and/or complete indication of an extent of the secondary backscatter radiation or backscatter condition can be assured. Alternatively, the backscatter indicia 150 can be distributed over a portion or separate portions of the DR detector 10 back surface. In one embodiment, the backscatter indicia 150 can be mounted to an outside surface of the DR detector 10.

FIG. 11A shows an active imaging area of a DR detector and an example secondary backscatter radiation indicia distribution according to embodiments of the application. As shown in FIG. 11A, the distribution of indicia 150 is symmetric, however, embodiments of the application are not intended to be so limited. For example, indicia 150 distributions can be linear, non-linear, aperiodic or asymmetric. In addition, placement of the backscatter detection capability can be chosen to not locate the backscatter indicia 150 directly under any electrical component. For example, it can be desirable to concentrate backscatter indicia 150 placement more towards the center of the DR detector 10, which can be the preferred location to image a particular anatomical region of the body for diagnosis.

FIG. 11B shows an active imaging area of a DR detector and another example secondary backscatter radiation indicia distribution according to embodiments of the application. Such an increased concentration of backscatter indicia 150' as shown in FIG. 11B toward a center or central region (e.g., round, rectangular) can be distributed according to a prescribed relationship relative to the active imaging area such as linearly distributed, non-linearly distributed, tiered, periodic, aperiodic or the like. An increased concentration can be correlated to components of the DR detector 10 such as but not limited to circuit boards or the like or other items such as AEC chambers. Thus, the distribution of the backscatter indicia 150, 150' need not be consistent throughout the DR detector 10. In one embodiment, the backscatter indicia 150, 150' can be distributed to be 1.5×, 2× or 5× denser in the center of the imaging area relative to an outer region of the imaging area, or a transition between the center and the outer region can be a gradual or tiered, linear or nonlinear increase toward the center.

FIG. 12 is a diagram that shows an exemplary secondary backscatter radiation indicia that can be reversed (e.g., removed from a backscatter absorbing material). In one embodiment, the primary backscatter layer 30 can include cutouts shaped to provide high contrast and be visually distinctive using such exemplary backscatter indicia shapes shown in FIG. 10. As shown in FIG. 12, the placement of exemplary backscatter indicia 220 cutouts is not intended to be limited to uniform distribution as shown in FIG. 12. In one embodiment, to provide for or insure reliable detection, the location of the backscatter indicia 220 does not correspond to or is preferably not partially or wholly correlated to any of the electrical or mechanical components.

FIG. 13 is a diagram that shows a simulated x-ray image exhibiting secondary backscatter artifacts caused by internal electrical components and backscatter indicia. As described herein, the density of the shadow produced by any particular component/indicia can depend on the material composition of that component. In some cases, the electrical components 28 may not produce a very pronounced shadow. Other components that have metal can produce a denser shadow, but still can be difficult to identify because of the item itself (e.g., the fine pitch of connector pins). Such slight shadows, denser shadows or aggregate shadows may or may not be a disadvantage or problem in a particular image (e.g., occur in a non-diagnostic region of the image).

In contrast to components of the DR detector 10, the secondary backscatter indicia 150, 150', 220 can be made very dense and large enough to distinctly or sufficiently stand out when secondary backscatter has occurred. As shown in FIG. 13, when backscatter indicia are distributed around the full detector image area, the backscatter indicia assure that the secondary backscatter condition is sampled over the full image.

Image processing can be applied to DR detector image data to reduce or remove dark current offsets, defective pixels and non-uniformity in gain. Using exemplary current hardware (e.g., processors) and software (e.g., computer technology image processing algorithms) that can process large amounts of data and produce results quickly (e.g., concurrently with examination, in real time such as less than a second or within seconds). Therefore, embodiments according to the application provide methods and or apparatus that can include image processing capability (e.g., execute image processing software algorithms) to analyze image data (e.g., from the DR detector 10) after each exposure that determine whether secondary backscatter radiation exists or determine whether any backscatter indicia shadows are detected in the image data. Fixed predefined locations of backscatter indicia 150, 150', 220 can aid in robust detection because the image data needs to be evaluated in selected or limited specific areas. Alternatively, a component image map (e.g., shown in FIG. 7) can also be used as an input to exemplary backscatter detection image processing units/apparatus/functions.

In one embodiment, when backscatter indicia are detected in the x-ray image data (e.g., using the DR detector image processor/image processing capability) by a radiographic imaging system, the technician can be alerted through a user's console in the radiographic imaging system. An exemplary alert can inform the technician that a secondary backscatter condition has occurred and/or that image artifacts have been detected that could compromise the ability to make an accurate diagnosis. Alternatively, an exemplary alert can inform the technician that the backscatter condition has occurred and also indicate on the x-ray preview image outlines of where possible artifacts might have occurred. Further, an additional exemplary alert can also input an indication into the x-ray image data (e.g., outside a medical diagnosis region) that a backscatter condition has occurred. In one embodiment, a displayed indication (e.g., dashed line 1300 shown in FIG. 13) around artifacts in the artifact map can indicate an estimate of a region of detected backscatter (e.g., over a threshold or within a prescribed distance to detected backscatter) within the entire image area.

Figure 14:
FIG. 14 is a diagram that shows an exemplary x-ray image exhibiting secondary backscatter artifacts and an alert regarding the same according to embodiments of the application.

FIG. 14 is a diagram that shows an exemplary x-ray image exhibiting secondary backscatter artifacts caused by internal electrical components and/or backscatter indicia and an alert regarding the same according to embodiments of the application. As shown in FIG. 14, an exemplary alert 1400 is positioned at a top region of the image. However, the positioning of the alert 1400 can be variable (e.g., image bottom, side) depending on the examination procedure or the alert 1400 can be generated just outside the imaging area or on a displayed representation of the x-ray image at an operator console. In contrast to FIG. 13, secondary backscatter radiation is detected throughout the x-ray image shown in FIG. 14.

Figure 15:
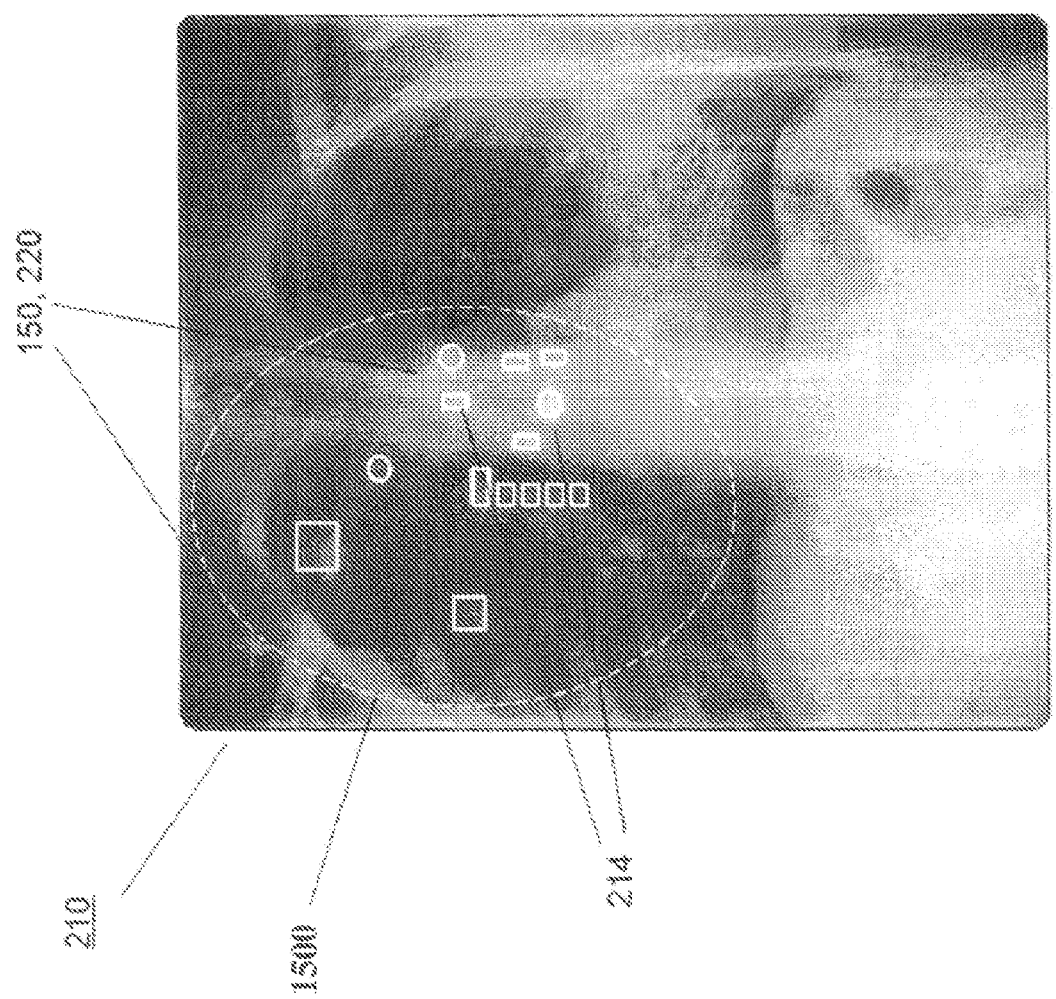
FIG. 15 is a diagram that shows an exemplary x-ray image exposed to backscatter radiation and an embodiment of backscatter indications generated in the image using a DR detector image processor according to the application.

FIG. 15 is a diagram that shows an x-ray image that has been exposed to backscatter radiation, where the backscatter condition has been detected by image processing of image data from the DR detector, and an indication is visually provided in a resulting image (e.g., displayed to the technician). As shown in FIG. 15, the technician can receive an image (e.g., a preview image) of the x-ray after (e.g., a few seconds) after the exposure has completed. In one embodiment, the operator's console can alert the operator that secondary backscatter has been detected. The operator can then either request an artifact map (e.g., artifact map 1500 (of cluster 200) shown in FIG. 15) with the image to indicate what areas are potentially affected or an artifact map (e.g., artifact map 1500) can then be displayed automatically in the image.

As shown in FIG. 15, white outlines can be superimposed around each of the electronic components 214 of cluster 200 to illustrate one exemplary embodiment of an image including an artifact map according to the application. Also, in FIG. 15, outlines can be shown for electrical components of one cluster, namely the cluster 200. Although backscatter indicia in the example of FIG. 15 have been distributed around the full DR detector image area, the backscatter indicia were detected in only a localized region of the image. As described herein, because secondary backscatter radiation can be non-uniform and realize an unpredictable distribution, often less than the full image area can be affected. Therefore, the artifact map of the electrical components in the vicinity of only the detected backscatter indicia can be displayed according to detection criteria on the preview image in FIG. 15. Displaying the detected secondary backscatter indicia and/or an indication of a range (e.g., indication 1300) of likely secondary backscatter based on the detected secondary backscatter indicia would allow the technician to make an improved decision whether to re-do the x-ray examination and expose the patient to another dose of ionizing radiation or use the existing x-ray image. When the technician knows that the upper region of the x-ray image shown in FIG. 15 is not needed for the diagnosis (e.g., body part of interest), then the x-ray image can be accepted, an optional notation regarding the secondary backscatter can be made and another exposure of the patient can be avoided.

In another embodiment, when the backscatter indicia are detected, an estimate of shadows caused by components in the DR detector and/or shadows caused by the backscatter indicia can be made and combined (e.g., subtracted, weighted and subtracted) with the original x-ray image data to provide the technician a "backscatter corrected image" (e.g., an additional image) using the image processing capacities of the DR detector or the radiographic imaging apparatus.

In one embodiment, the secondary backscatter condition, the image overlay showing potential areas where artifacts may be present, and/or the backscatter corrected image can be incorporated into the image as metadata, which can be used subsequently with the corresponding x-ray image or image data (e.g., radiologists/doctors downstream for diagnosis).

Exemplary embodiments of secondary backscatter radiation indicia, DR detectors, radiographic imaging apparatus, and/or methods using the same have various advantages. For example, embodiments described herein can include specially shaped secondary backscatter indicia added to a DR detector. Such exemplary shaped backscatter indicia can be detected by computer operable image processing procedures applied to the image data and optionally used to (i) inform the x-ray technician immediately after the x-ray exposure that a secondary backscatter condition has occurred or (ii) present an image with backscatter information/characteristics highlighted and/or (iii) provide an image with backscatter artifacts reduced or corrected. Distinctive shapes can readily differentiate backscatter indicia shadows from shadows caused by detector components or body parts of a patient.

In one embodiment, functions of the specially shaped backscatter indicia can be realized by using actual electrical component (e.g., component image map) or the shadows (e.g., image data) from the actual electrical components in the DR detector 10. As described herein, such component shadow information can be ascertained from information derived from a component image map and corresponding raw/corrected image data.

It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

As will be appreciated by one skilled in the art, the present invention may be embodied as a system, method, or computer program product. Accordingly, an embodiment of the present invention may be in the form of an entirely hardware embodiment, an entirely software embodiment (including firmware, resident software, micro-code, and other suitable encodings) or an embodiment combining software and hardware aspects that may all generally be referred to herein as a "circuit" or "system." Furthermore, the present invention may take the form of a computer program product embodied in a computer-readable storage medium, with instructions executed by one or more computers or host processors. This medium may comprise, for example: magnetic storage media such as a magnetic disk (such as a hard drive or a floppy disk) or magnetic tape; optical storage media such as an optical disc, optical tape, or machine readable bar code; solid state electronic storage devices such as solid state hard drives, random access memory (RAM), or read only memory (ROM); or any other physical device or medium employed to store a computer program. The computer program for performing the method of the present invention may also be stored on computer readable storage medium that is connected to a host processor by way of the internet or other communication medium.

Those skilled in the art will readily recognize that the equivalent of such a computer program product may also be constructed in hardware. The computer-usable or computer-readable medium could even be paper or another suitable medium upon which executable instructions are printed, as the instructions can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport computer instructions for use by, or in connection with, an instruction execution system, apparatus, or device.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for identifying secondary backscatter in image data from a digital radiography (DR) detector including a housing configured with first and second surfaces and at least one wall to connect the first and second surfaces, the method comprising:
   exposing a DR detector to x-ray flux passing through the first surface;
   obtaining image data from the DR detector to form an electronic radiographic image corresponding to received x-ray flux;
   detecting representations of secondary backscatter indicia in the image data based on at least one characteristic of the secondary backscatter indicia in the DR detector, the representations of secondary backscatter indicia resulting from reflected x-ray flux passing through a portion of the housing other than the first surface; and
   outputting a signal responsive to detecting a secondary backscatter condition when the representations of the secondary backscatter indicia in the image data exceed a threshold.

2. The method of claim 1, comprising providing an indicator of the secondary backscatter condition to an operator, at an operator console, in a non-diagnostic portion of the electronic radiographic image, using a component image map, in a first image within a prescribed distance of the detected secondary backscatter indicia, or in a second image where the representations of the secondary backscatter indicia have been reduced or removed.

3. The method of claim 1, where the secondary backscatter indicia have a prescribed arrangement within the DR detector, where the secondary backscatter indicia include a radiation absorbing material configured to produce a high contrast shadow image in an x-ray image when secondary backscatter radiation is generated.

4. The method of claim 3, where the secondary backscatter indicia include electronic components in the DR detector.

5. The method of claim 3, comprising:
   providing a first plurality of backscatter elements and a second plurality of backscatter elements including the same x-ray absorption characteristics;
   detecting when backscatter indicia shadows are present and over a prescribed threshold level in the image data based on prescribed locations and the x-ray absorption characteristics of the first plurality of backscatter elements and the second plurality of backscatter elements, and based on known positions of electronic components in the DR detector; and
   providing a backscatter corrected image having the detected backscatter indicia shadows reduced below the threshold in the image data.

6. The method of claim 1, where the secondary backscatter indicia include a prescribed arbitrary shape, where the prescribed arbitrary shape includes visually distinctive shape relative to an object being imaged or relative to components of the DR detector.

7. The method of claim 1, comprising providing a primary backscatter absorbing component positioned below the detector array, where the secondary backscatter indicia are positioned above or below the primary backscatter absorbing component or the secondary backscatter indicia include a different x-ray absorbing characteristic relative to the primary backscatter absorbing component and are incorporated into the primary backscatter absorbing component.

8. A method for modifying a digital flat panel radiographic detector including a housing configured with first and second surfaces and a plurality of walls to form a cavity, a radiographic image detector mounted within the cavity to convert a radiographic image to an electronic radiographic image, the detector comprising a detector array; the method comprising:
  detecting a plurality of secondary backscatter indicia distributed in a prescribed arrangement in the cavity using positions of the secondary backscatter indicia and image data used to form the electronic radiographic image, where each of the plurality of backscatter indicia include an arbitrary shape that is different from an object being imaged or electronic components used in the radiographic detector.

9. The method of claim 8, comprising adding the plurality of secondary backscatter indicia in the prescribed arrangement to the digital flat panel radiographic detector.

10. A digital radiography detector comprising:
  a housing having first and second surfaces and a plurality of walls to form a cavity;
  a radiographic image detector mounted within the cavity to convert a radiographic image to an electronic radiographic image, the detector comprising a detector array formed on a substrate;
  a plurality of backscatter indicia distributed in a prescribed arrangement in the cavity, where the plurality of backscatter indicia are configured to produce a high contrast shadow image in the electronic radiographic image; and
  an image processor to evaluate the electronic radiographic image to detect representations of the secondary backscatter indicia that include a prescribed shape to generate a signal when the representations of the secondary backscatter indicia are detected at a prescribed level.

11. The digital radiography detector of claim 10, where the first surface of the housing is over the radiographic image detector and the secondary backscatter radiation is reflected x-ray flux passing through a portion of the housing other than the first surface.

12. The digital radiography detector of claim 10, where the plurality of backscatter indicia include a prescribed arbitrary shape.

13. The digital radiography detector of claim 12, where each of the plurality of backscatter indicia include the prescribed arbitrary shape, where the prescribed arbitrary shape is visually distinctive shape relative to an object being imaged or the prescribed arbitrary shape.

14. The digital radiography detector of claim 12, where the backscatter indicia have an x-ray attenuation characteristic related to an x-ray attenuation characteristic of a selected electronic component, the backscatter indicia have an x-ray attenuation characteristic greater than electronic components in the cavity.

15. The digital radiography detector of claim 12, the plurality of backscatter indicia comprising:
  a first plurality of backscatter elements;
  a second plurality of backscatter elements including a different absorption characteristic from the first plurality of backscatter elements;
  an image processor to detect when backscatter indicia are over a prescribed threshold level in the image data based on prescribed locations and x-ray absorption characteristics of the first plurality of backscatter elements and the second plurality of backscatter elements and to provide in a corresponding image a representation that secondary backscatter was detected.

16. The digital radiography detector of claim 10, comprising a second backscatter absorbing material positioned below the detector array,
  where the backscatter indicia are positioned above or below the second backscatter absorbing material in the cavity, or the backscatter indicia include a different x-ray absorbing characteristic relative to the second backscatter absorbing material and are incorporated into the second backscatter absorbing material.

17. The digital radiography detector of claim 10, where the secondary backscatter indicia include electronic components in the DR detector.

18. The digital radiography detector of claim 10, where the backscatter indicia are evenly distributed in relation to an active imaging area, are distributed according to a prescribed relationship in relation to the active imaging area, are distributed corresponding to an arrangement of electronic components below the active imaging area, or are distributed to increase in number or density in a center region relative to an outer region of the active imaging area.

19. The digital radiography detector of claim 10 where the radiographic image detector further comprises:
  a scintillator screen disposed on a side of the detector array for converting a radiographic image into a radiographic light image which is converted by the detector array into the electronic radiographic image;
  a stiffener disposed in the cavity;
  a shock absorbing assembly comprising an elastomeric material and located within the cavity for absorbing shock to the detector array/stiffener in directions perpendicular to and parallel to the detector array/stiffener;
  a wireless interface having an antenna for wirelessly transmitting an electronic radiographic image from the detector to a remote location; and
  a battery and imaging electronics mounted within the cavity below the detector array/stiffener,
  wherein the housing includes a detachable external frame including four side walls.

20. A method for identifying secondary backscatter in image data from a digital radiography (DR) detector including a housing configured with first and second surfaces and at least one wall to connect the first and second surfaces, the method comprising:
  exposing a DR detector to x-ray flux passing through the first surface;
  obtaining image data from the DR detector to form an electronic radiographic image corresponding to received x-ray flux;
  detecting representations of secondary backscatter indicia in the image data based on at least one characteristic of the secondary backscatter indicia in the DR detector;
  detecting a secondary backscatter condition when the representations of the secondary backscatter indicia in the image data exceed a threshold; and
  providing an indicator of the secondary backscatter condition to an operator, at an operator console, in a non-diagnostic portion of the electronic radiographic image, in a first image within a prescribed distance of the detected secondary backscatter indicia, or in a second image where the representations of the secondary backscatter indicia have been reduced or removed.

* * * * *